United States Patent
Lopez et al.

[19]

[11] Patent Number: 5,954,708
[45] Date of Patent: Sep. 21, 1999

[54] MEDICAL CONNECTOR

[75] Inventors: George A. Lopez, Huntington Beach; Virgil R. Laul, Dana Point, both of Calif.

[73] Assignee: ICU Medical, Inc., San Clemente, Calif.

[21] Appl. No.: 09/056,974

[22] Filed: Apr. 8, 1998

Related U.S. Application Data

[63] Continuation of application No. 08/473,524, Jun. 7, 1995, Pat. No. 5,776,116, which is a continuation of application No. 08/424,237, Apr. 19, 1995, abandoned, which is a continuation of application No. 08/279,247, Jul. 21, 1994, abandoned, which is a continuation of application No. 08/020,098, Feb. 19, 1993, Pat. No. 5,344,414, which is a continuation of application No. 07/346,193, Jan. 9, 1997, abandoned, which is a division of application No. 06/606,679, May 3, 1984, abandoned, which is a continuation-in-part of application No. 06/543,248, Oct. 19, 1983, abandoned, which is a continuation-in-part of application No. 06/460,585, Jan. 24, 1983, abandoned.

[51] Int. Cl.$^6$ .................................................. A61M 25/00
[52] U.S. Cl. ............................ 604/533; 604/535; 604/905
[58] Field of Search ..................................... 604/533, 534, 604/535, 538, 539, 905

[56] References Cited

U.S. PATENT DOCUMENTS

| | | |
|---|---|---|
| 1,578,517 | 4/1926 | Heim . |
| 2,210,098 | 8/1940 | Ravenscroft . |
| 2,999,499 | 9/1961 | Willet . |
| 3,134,380 | 5/1964 | Armao . |
| 3,502,097 | 3/1970 | Muller . |
| 3,630,199 | 12/1971 | Gangarosa et al. . |
| 3,797,486 | 3/1974 | Shaps . |
| 3,861,388 | 1/1975 | Vaughn . |
| 3,974,832 | 8/1976 | Kruck . |
| 3,976,073 | 8/1976 | Quick et al. . |
| 3,986,508 | 10/1976 | Barrington . |
| 3,994,293 | 11/1976 | Ferro . |
| 4,005,710 | 2/1977 | Zeddies et al. . |
| 4,019,512 | 4/1977 | Tenczar . |
| 4,040,420 | 8/1977 | Speer . |
| 4,128,098 | 12/1978 | Bloom et al. . |
| 4,149,535 | 4/1979 | Volder . |
| 4,161,949 | 7/1979 | Thanawalla . |
| 4,187,846 | 2/1980 | Lolachi et al. . |
| 4,191,183 | 3/1980 | Mendelson . |
| 4,214,779 | 7/1980 | Losell . |
| 4,219,912 | 9/1980 | Adams . |
| 4,257,416 | 3/1981 | Prager . |
| 4,294,249 | 10/1981 | Sheehan et al. . |
| 4,296,949 | 10/1981 | Muetterties et al. . |
| 4,306,705 | 12/1981 | Svensson . |
| 4,328,802 | 5/1982 | Curley et al. . |
| 4,329,987 | 5/1982 | Rogers et al. . |
| 4,334,551 | 6/1982 | Pfister . |
| 4,338,933 | 7/1982 | Bayard et al. . |
| 4,362,156 | 12/1982 | Feller, Jr. et al. . |
| 4,405,163 | 9/1983 | Voges et al. . |
| 4,432,765 | 2/1984 | Oscarsson . |
| 4,439,193 | 3/1984 | Larkin . |
| 4,457,749 | 7/1984 | Bellotti et al. . |

(List continued on next page.)

FOREIGN PATENT DOCUMENTS

| | | |
|---|---|---|
| 1105959 | 7/1981 | Canada . |
| 0 114 677 | 10/1983 | European Pat. Off. . |
| 84 25 197 U | of 1985 | Germany . |

*Primary Examiner*—John D. Yasko
*Attorney, Agent, or Firm*—Knobbe, Martens, Olson & Bear, LLP

[57] ABSTRACT

Disclosed is a connector for introducing medication into a patient in a safe, convenient way. It comprises a pair of plastic tubular members adapted to be manually pushed together to engage in a male-female relationship, and a locking mechanism that detachably secures the members together. The male member has a sealed entry port at its end, and the female member safely houses within it a needle which centrally pierces the seal of the port upon engagement of the members. Preferably, the locking mechanism provides a "click" sound when it locks the members together.

7 Claims, 9 Drawing Sheets

U.S. PATENT DOCUMENTS

| | | |
|---|---|---|
| 4,508,367 | 4/1985 | Oreopoulos et al. . |
| 4,511,359 | 4/1985 | Vaillancourt . |
| 4,512,766 | 4/1985 | Vaillancourt . |
| 4,564,054 | 1/1986 | Gustavsson . |
| 4,607,868 | 8/1986 | Harvey et al. . |
| 4,617,012 | 10/1986 | Vaillancourt . |
| 4,645,494 | 2/1987 | Lee et al. . |
| 4,673,400 | 6/1987 | Martin . |
| 4,725,267 | 2/1988 | Vaillancourt . |
| 4,752,292 | 6/1988 | Lopez et al. . |
| 4,846,809 | 7/1989 | Sims . |
| 4,917,668 | 4/1990 | Haindl . |
| 4,932,944 | 6/1990 | Jagger et al. . |
| 4,946,445 | 8/1990 | Lynn . |
| 4,964,855 | 10/1990 | Todd et al. . |
| 4,981,469 | 1/1991 | Whitehouse et al. . |
| 4,998,713 | 3/1991 | Vaillancourt . |
| 4,998,921 | 3/1991 | Vickroy et al. . |
| 5,069,225 | 12/1991 | Okamura . |
| 5,100,394 | 3/1992 | Dudar et al. . |
| 5,122,123 | 6/1992 | Vaillancourt . |
| 5,153,489 | 10/1992 | Jepson et al. . |
| 5,158,554 | 10/1992 | Jepson et al. . |
| 5,167,648 | 12/1992 | Jepson et al. . |
| 5,171,234 | 12/1992 | Jepson et al. . |
| 5,188,620 | 2/1993 | Jepson et al. . |
| 5,195,992 | 3/1993 | Dudar et al. . |
| 5,199,947 | 4/1993 | Lopez et al. . |
| 5,290,254 | 3/1994 | Vaillancourt . |
| 5,344,414 | 9/1994 | Lopez et al. . |

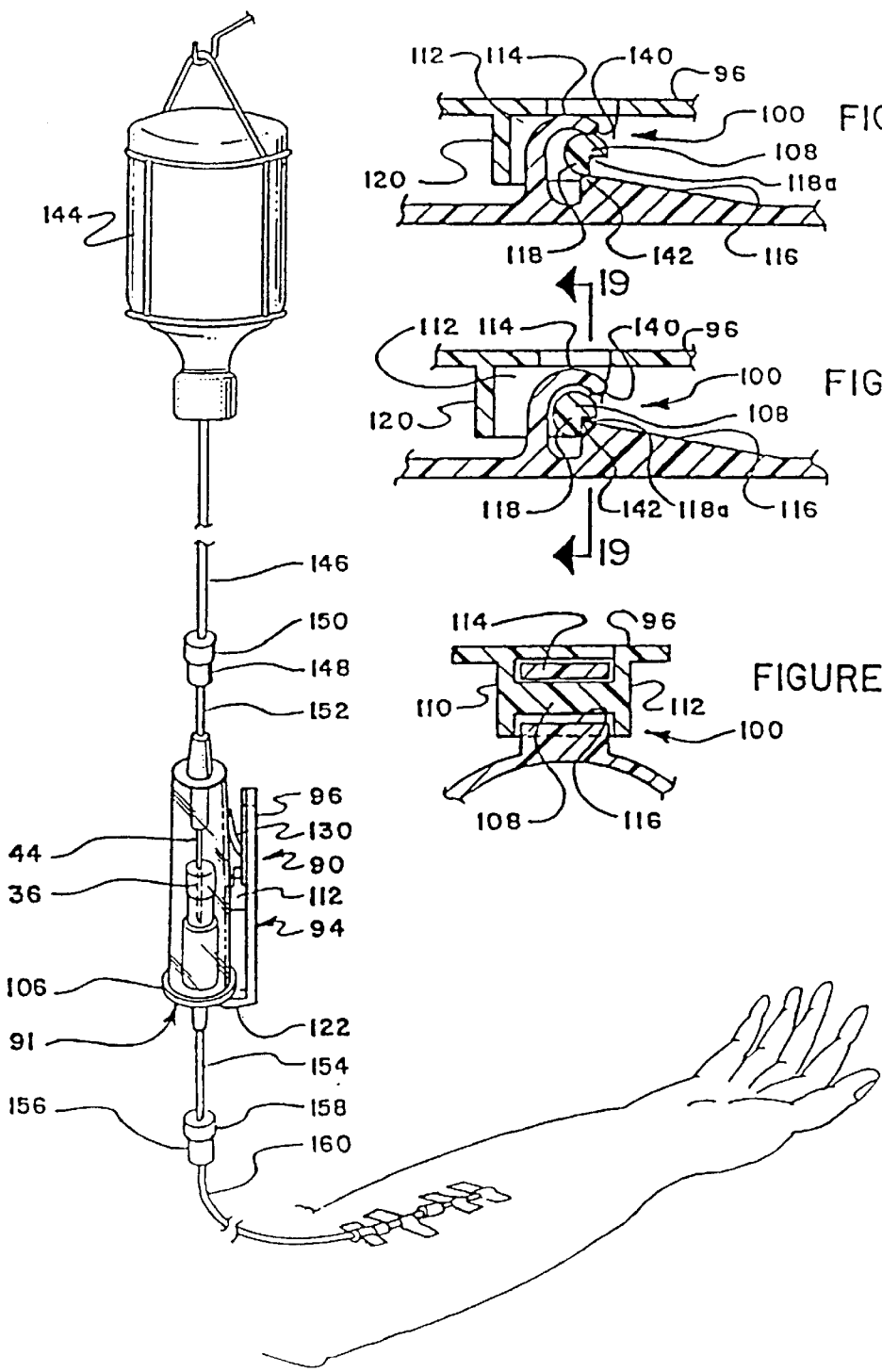
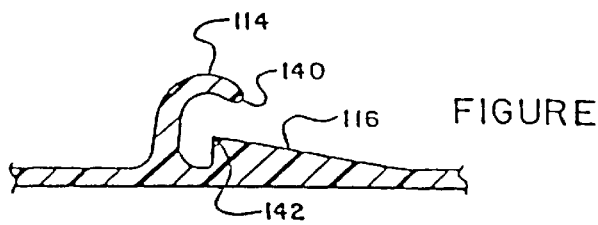
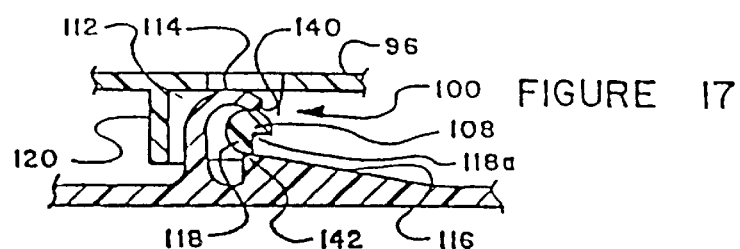
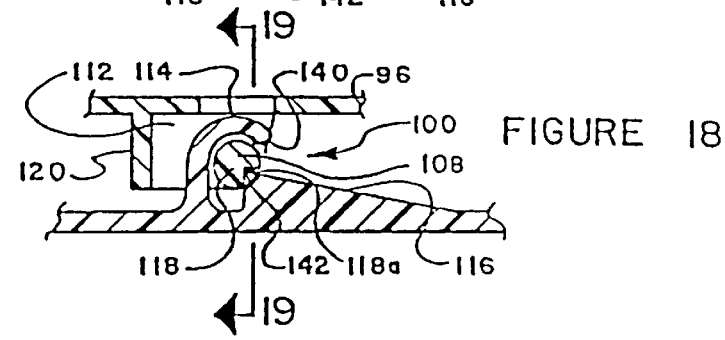
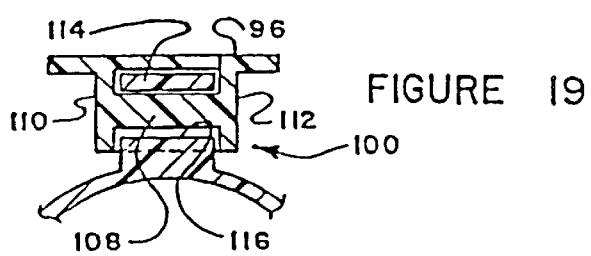

MEDICAL CONNECTOR

RELATED PATENT APPLICATIONS

"This application is a continuation of U.S. patent application Ser. No. 08/473,524, filed Jun. 7, 1995, now U.S. Pat. No. 5,776,116 which was a continuation of U.S. patent application Ser. No. 08/424,237, filed Apr. 19, 1995, now abandoned which was a file wrapper continuation of U.S. patent application Ser. No. 08/279,247, filed Jul. 21, 1994, now abandoned which was a continuation of U.S. patent application Ser. No. 08/020,098, filed Feb. 19, 1993, now issued U.S. Pat. No. 5,344,414, which was a continuation of U.S. patent application Ser. No. 07/346,193. filed Jan. 9, 1987, now abandoned which was a divisional of U.S. patent application Ser. No. 06/606,679, filed May 3, 1984, now abandoned, which was a continuation-in-part of U.S. patent application Ser. No. 06/543,248, filed Oct. 19, 1983, now abandoned, which was a continuation-in-part of U.S. patent application Ser. No. 06/460,585, filed Jan. 24, 1983, now abandoned." These previously filed patent applications, which are incorporated herein by reference and made part of this patent application, disclose the experimental versions of this invention. These experimental versions are also disclosed herein.

BACKGROUND OF THE INVENTION

1. Field of the Invention

This invention relates to medical connectors used in the treatment of the injured or sick, and in particular to a connector for introducing medication into a patient in a safe, convenient way.

2. Background Discussion

It is a common practice in treating patients, particularly patients who must be cared for under emergency conditions, with medication introduced into the patient intravenously. An intravenous solution, commonly referred to as parenteral liquid, is fed from a container holding this liquid. The liquid flows through tubing into a needle which has been inserted into the patient's vein. The needle is taped securely to the patient's body and is not likely to pull loose if the patient moves. Medication needed to sustain the life of the patient, for example, drugs which maintain the blood pressure of the patient at the desired level, are added to the parenteral liquid. The conventional practice is to introduce the medication through a second needle inserted into a sealed entry port in the tubing through which the parenteral liquid flows.

One problem with this conventional practice is that the needle may be pulled loose from the sealed port relatively easily. Such accidental removal of the needle from the sealed port can have very serious consequences and could even lead to the death of the patient. Although many hospitals require nurses to tape the needle securely to the tubing, this is not always done, because taping is a burdensome and time consuming task.

A second problem with the conventional practice is needle sticks. From time to time a nurse in attempting to insert the needle into the sealed entry port will accidentally stick himself or herself with the needle. This often occurs under emergency conditions when the nurse is under pressure to complete this task as quickly as possible. Not only is the accomplishment of the task delayed, but the nurse must stop working and have a blood test performed. Such a test is needed in case the nurse becomes infected, because the hospital will be responsible financially. Consequently, needle sticks not only result in increased hospital cost, but are a possible life treating event to the nurse.

A third problem with the conventional practice is infection. All too often a patient's life is seriously endangered by bacteria gaining entry into a patient's blood stream and infecting the patient. In a vast number of cases it is unknown how the bacteria gain entry. We have observed conditions in hospitals and identified that one likely way the bacteria gain entry is by contamination of the needle inserted into the sealed entry port. This happens when the nurse notices that the needle has been pulled loose and simply reinserts it even though it may now have on its surface bacteria picked up by direct contact with, for example, the patient's bedding. Another possible way that bacteria may gain entry into the patient's blood stream is through contamination of the tape used to hold the needle to the connector.

MAJOR FEATURES OF THE INVENTION

The problems discussed above present a serious health hazard to patients and their nurses. The present invention eliminates these problems and provides a medical connector which is both safe and convenient to use.

There are several features of this invention which contribute to its safety and convenience, no single one of which is solely responsible for these desirable attributes. Many of these features were present in our experimental versions of the invention, which were improved after testing. Without limiting the scope of this invention as expressed by the claims, its more prominent features will now be discussed briefly. After considering this discussion, and particularly after reading the section of this application entitled DETAILED DESCRIPTION OF THE DRAWING, one will understand how the features of this invention provide the attributes of safety and convenience.

One safety feature of this invention is the use of a cap member to enclose the needle to be inserted into the sealed entry port structure. This cap member fits snugly over the entry port structure, connecting with the port structure in a male-female mating relationship. The needle pierces the seal when the cap member is seated on the port structure. This needle is housed deep within a cavity in the cap member that terminates in an open mouth into which the sealed end of the port structure fits. This open mouth is narrow in width so that the finger of the nurse or patient cannot fit into the cavity and contact the needle. Since the needle is so mounted within the cap member, the likelihood of bacterial contamination is avoided or reduced and the nurse is protected against accidental needle sticks.

A second safety feature is provided by the wall design of the cap member and port structure. These walls are of preferably cylindrical configuration and engage each other like a telescope. The interior surface of the wall of the cap member slides over the exterior surface of the wall of the mating port structure, with these walls engaging each other to guide the needle into the center of the seal. This ensures that the needle does not scrape against the inside surface of the wall of the port structure. Particles scraped from this wall could make their way into the patient's blood stream and result in death. This potentially lethal condition is inherent in the design of conventional devices. But the connector of this invention, with the guideway wall design of the cap member and port structure, ensures that the needle is directed into the center of the seal so that it avoids scraping against the inside surface of the wall of the port structure. This guideway wall design also permits the nurse quickly to connect the cap member to the port structure. This makes the connector of this invention not only more convenient to use, but in emergencies, enables the nurse to administer medication to a patient faster than with conventional devices and doing it without the danger of needle sticks.

A third safety feature of the invention is that a locking mechanism detachably secures the cap member to the port structure. Because of this feature, movement of the patient does not result in accidental removal of the needle from the seal. Although many different types of locking mechanisms may be employed, the preferred one provides a sound upon locking engagement of the cap member and port structure. We have devised such a locking mechanism which produces a sound such as a "click." This "click" is an audible signal which tells the nurse that the cap member is locked safely to the port structure and cannot be accidentally jarred loose by movement of the patient.

Several embodiments of the invention illustrating all the features of this invention will now be discussed in detail. These embodiments show the invention being used for administering medication intravenously to a patient. This invention may also be used to administer medication to a patient in other ways, for example, intracranially or intraperitonially.

BRIEF DESCRIPTION OF THE DRAWING

The drawing, wherein like numerals indicate like parts, depicts four embodiments of this invention in which:

FIG. 16 is an enlarged cross-sectional view of a portion of the hinge of the locking mechanism.

FIG. 17 is an enlarged cross-sectional view of the position of the handle just prior to being secured to the cap member.

FIG. 18 is a cross-sectional view similar to that shown in FIG. 17 depicting the handle coupled to the cap member.

FIG. 19 is a cross-sectional view taken along line 19—19 of FIG. 18.

FIG. 20 is a perspective view showing the medical connector of FIG. 7 having one end coupled to a tube extending from a patient's arm and another end coupled to a tube extending from a container holding medication.

DETAILED DESCRIPTION OF THE DRAWING

Conventional Connector System

Figure 1:
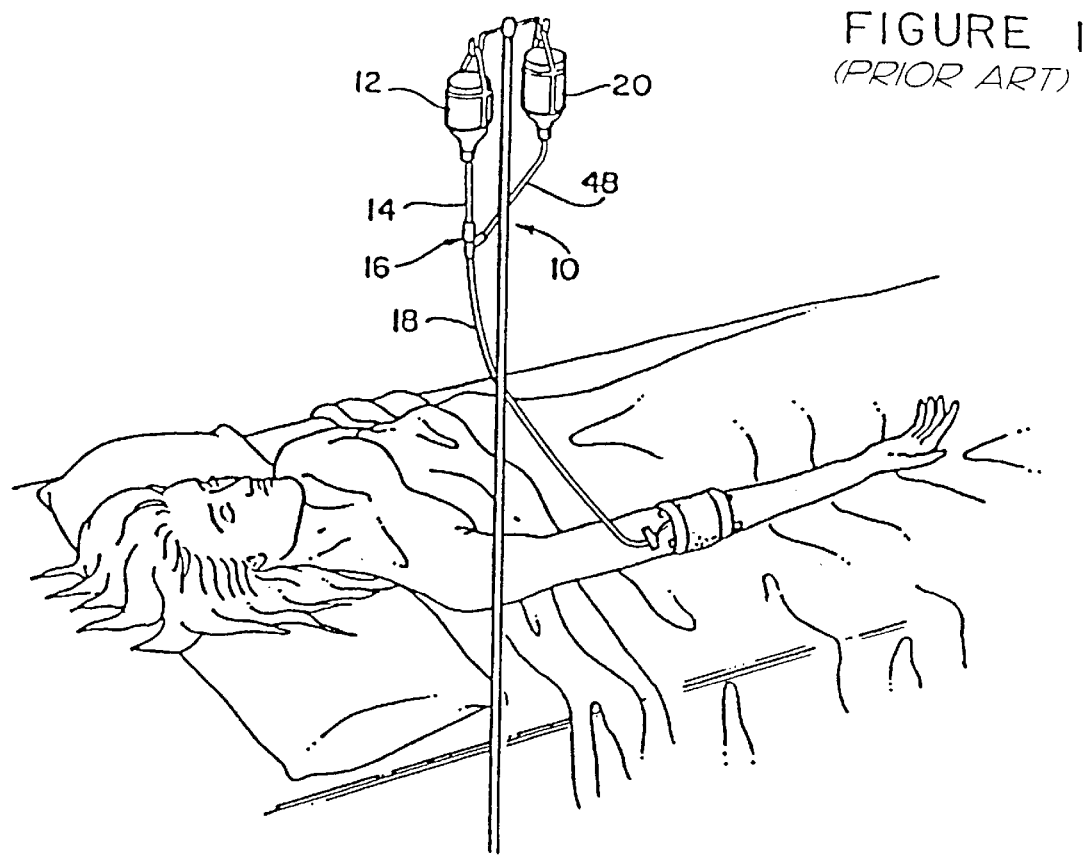
FIG. 1 is a schematic view illustrating administering medication intravenously to a patient in accordance with conventional practice.
Figure 2:
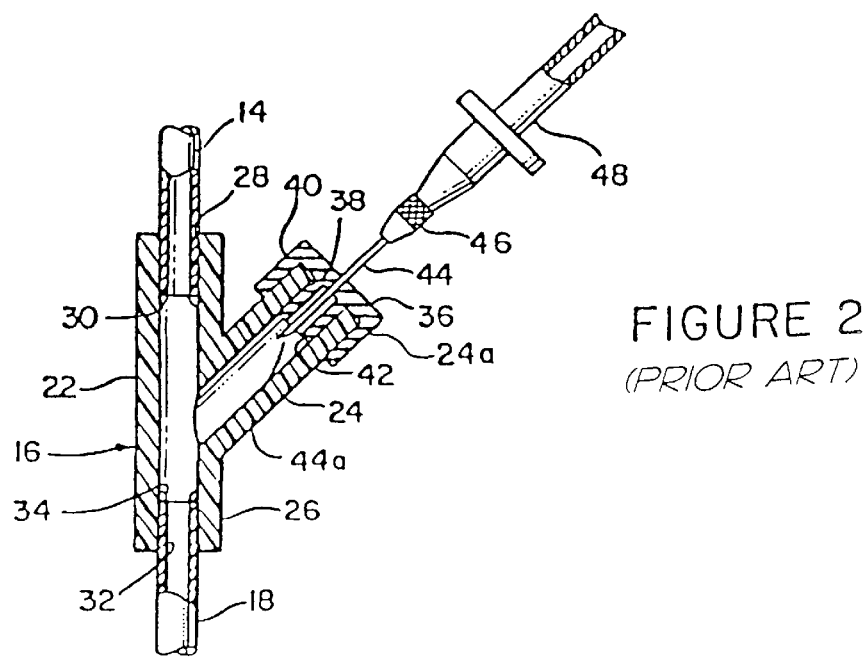
FIG. 2 is a cross-sectional view of a piggyback connector for introducing parenteral liquid and medication intravenously to the patient shown in FIG. 1.

As shown in FIGS. 1 and 2, the current way of intravenously introducing parenteral liquid into a patient is by the conventional feeding system 10. This feeding system 10 includes a container 12 for the parenteral liquid, a tube 14 extending from the container and connected to a Y or "piggyback" connector 16, and a tube 18 from the piggyback connector to a needle (not shown) inserted into a vein of the patient. The needle is taped to the patient so that movement of the patient will not result in the needle being pulled from the patient's vein.

As best illustrated in FIG. 2, medication from the container 20 is introduced through the piggyback connector 16 into the parenteral liquid flowing through the feeding system 10. This piggyback connector 16 consists of two tubular conduits 22 and 24 which merge into a third tubular conduit 26. The tubing 14 from the container 12 of parenteral liquid is inserted into the inlet port 28 of the conduit 22 and secured in position, for example, by an adhesive which bonds the external surface of this tube to the internal wall surface of the conduit. There is a stop 30 which limits the extent to which this tube 14 can be inserted into the conduit. In a similar fashion, the tube 18 is secured to the outlet port 32 of the piggyback connector. This tube 18 is inserted into the outlet port 32 until it abuts a stop 34 in the internal wall of the conduit. This tube 18 is secured by an adhesive to the internal wall of the conduit 26.

The sealed entry port structure of the conventional feeding system 10 is provided by the branch conduit 24 which has a standard latex rubber seal 36 at its inlet port 38 to seal this port. Consequently, bacteria cannot enter the piggyback connector 16 via the inlet port 38 because of the seal 36. This seal 36 is of conventional design and includes coaxial annular aprons 40 and 42 which fit over the conduit wall 24a and grip the external and internal wall surfaces to hold the seal securely to the conduit 24. A suitable seal may be obtained from the West Company of Phoenixville, Pa.

The medication is introduced into the parenteral liquid flowing through the piggyback connector 16 by a needle 44 which is inserted through the central part of the seal 36 into the branch conduit 24. This needle 44 is connected by a suitable connector 46 to a tube 48 which is connected to the container 20 (FIG. 1) for the medication. As parenteral liquid flows through the piggyback connector 16 into the inlet port 28 and out the outlet port 32, the medication is drawn into this stream of liquid, flowing from the container 20 via the tube 48 and through the open tip or end 44a of the needle 44 into the parenteral liquid.

After studying FIGS. 1 and 2, the several problems associated with the conventional practice can now be more fully understood. If the patient moves, for example, rolls or moves his or her arm, the needle 44 may be pulled from the seal 36. If this occurs, the latex seal 36 has sufficient resiliency to close off the hole in the seal produced by the needle 44. The parenteral liquid will continue to flow into the patient's system, but the necessary medication is no longer being introduced into it. The consequences of this condition are very grave and, if this condition is unnoticed by the nurse, it could result in the death of the patient or serious complications in the patient's treatment. Even if the nurse notices that the needle 44 has been removed from the seal 36 and reinserts it into the seal, it is possible that the needle has been contaminated with bacteria. The use of such a contaminated needle 44 is unacceptable, but nevertheless this sometimes happens. The needle 44 may be taped to the conduit 24, and many hospitals instruct nurses to do this. When this task is done, the needle 44 is secured, but cannot be conveniently removed and then reinserted. And even when taping the needle 44, if this is not done carefully, the needle may still be contaminated by the nurse touching the needle or the tape being contaminated. Also, because the nurse holds the conduit 24 with one hand while inserting the needle 44, the nurse may accidentally stick the needle directly into the hand holding this conduit, or stick the needle through the conduit wall 24a into this hand.

These problems associated with the conventional practice are eliminated by the several different embodiments of this invention disclosed hereinafter.

First Embodiment of the Invention

Figure 3:
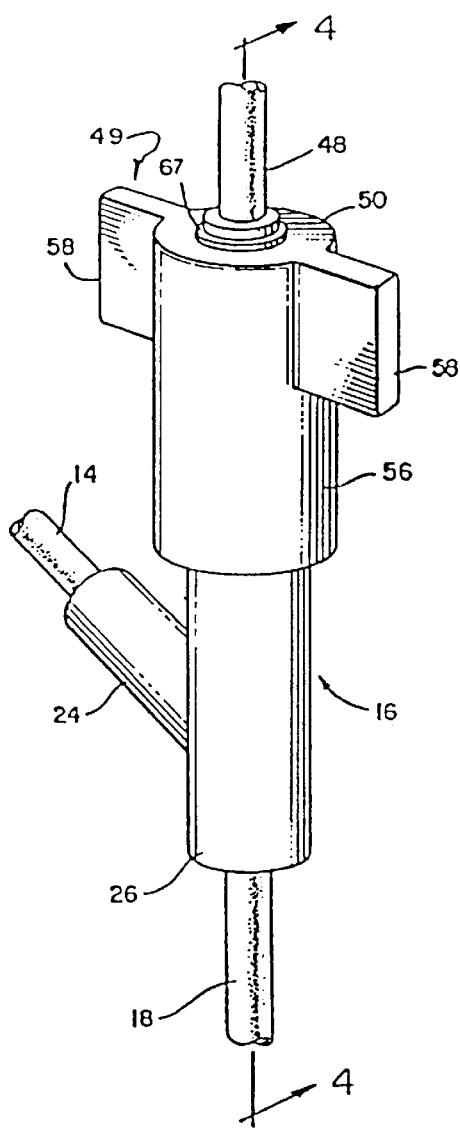
FIG. 3 is a perspective view of the first embodiment of the medical connector of the present invention which employs a slip-on/ twist lock type means for securing the cap member to the port structure.
Figure 4:
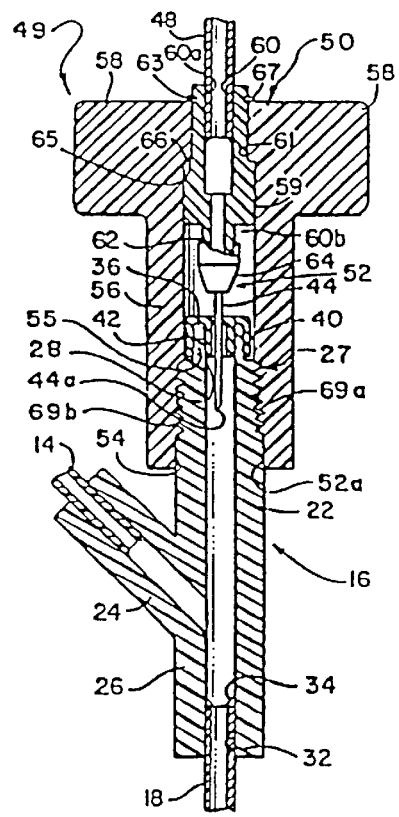
FIG. 4 is a cross-sectional view of the connector shown in FIG. 3 taken along line 4—4 of FIG. 3.

As illustrated in FIGS. 3 and 4, the first embodiment of this invention, connector 49, employs a cap member 50 housing deep within the needle 44. As will be discussed in greater detail hereinafter, the cap member 50 is secured by a slip-on/twist lock type of locking mechanism to the piggyback connector 16 so that movement of the patient does not result in the needle 44 being pulled from the seal 36. The parenteral liquid is introduced via the conduit 24, and the conduit 22 carry the seal 36 that covers the inlet port 28. In this embodiment, this sealed conduit 28 constitutes the entry port structure 27. The cap member 50 is detachably secured to the entry port structure 27, with the needle 44 penetrating the center of the seal 36 when the cap member 50 mates with the port structure 27.

Figure 4A:
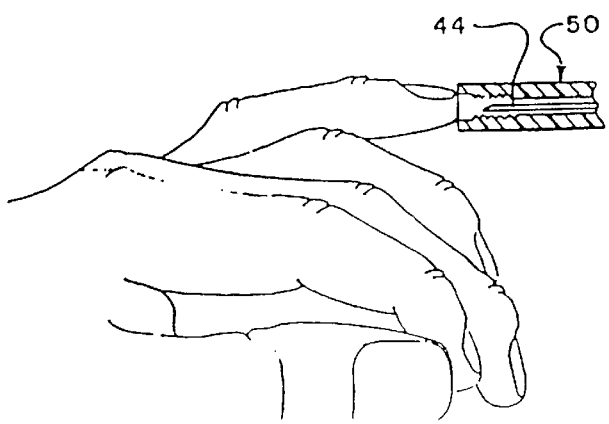
FIG. 4a is a perspective view showing how the cap member prevents needle sticks.

The cap member 50 comprises a cylindrical connector section 56 having a hollow interior forming the chamber or cavity 52 housing the needle 44. This needle 44 is disposed lengthwise along the longitudinal axis of the cavity 52 and is centrally located. The cavity 52 has an open mouth 52a which allows the cap member to be seated over the port structure 27. The mouth 52a, however, is constricted so that, as illustrated in FIG. 4a, it prevents the little finger of a typical adult user from being inserted into the cavity 52. The tip or end 44a of the needle is safely displaced inwardly from the open mouth 52a so that even if the user intentionally inserted his or her finger into the open mouth, the tip of the needle would not stick this finger. Typically, the open mouth 52a has a maximum width of no greater than about one centimeter, and the minimum distance between the mouth 52a and the tip 44a is about one centimeter.

The locking mechanism includes the threads 69a formed in the end 54 of the interior cavity wall 55 and the threads 69b in the exterior wall of the conduit 22. These threads 69a and 69b engage upon connection of the cap member 50 to the port structure 27 by screwing the cap member to the conduit 22. The top of the cap member 50 has a pair of outwardly extending wings 58 which facilitate screwing the cap member 50 to the conduit 22. As this is done, the interior wall 55, sliding over the exterior surface of the conduit 22, guides the needle 44 so that it penetrates the center of the seal 36. To further ensure that the needle 44 penetrates the center of the seal 36, the threads 69b could be lowered further beneath the seal so that the cap member would fit telescopically over the conduit 22 and then be screwed into position. Thus, the cap member 50, serving as the female component, and conduit 22, serving as the male component, mate in a male-female relationship, with the needle 44 always being housed safely within the center of the cavity in an unexposed condition and positioned to pierce the center of the seal 36.

A spindle 59 is provided to enable the cap member 50 to be screwed onto the port structure 27 without twisting the tube 48. This spindle 59 is received within an opening 61 within the cap member 50. The body of the spindle 59 has a cylindrical neck section with a groove 63 in an end which protrudes from the opening 61. The cylindrical body expands outwardly slightly to provide a shoulder 65 which engages a stop 66 when the spindle 59 is placed in the opening, and a TRU seal C-ring 67 is received in the groove 63 to hold the spindle in position but allowing the cap member to revolve about the spindle as it is screwed onto the port structure 27.

Along the longitudinal axis of the spindle 59 is a passageway 60. The tube 48 from the container 20 holding the medication is inserted into the one end 60a of the passageway 60 and is bonded to the internal surface of this passageway, for example, by means of an adhesive. The other end 60b of the passageway terminates in a threaded connector section 62 to which the needle 44 is secured. This needle has an adapter 64 which has an internal thread which engages the threads of the connector section 62. The needle 44 extends outwardly from this adapter 64. Thus, the needle 44 is held secure to the piggyback connector 16, penetrating the center of the seal 56 with its point 44a safely displaced away from the inside wall 55 of the conduit 22.

This connector 49 embodies many of the features of this invention. For example, the cap member 50 safely houses the needle 44, and the threads on the guiding walls provide means for detachably securing the cap member to the port structure without taping. But it has several components, and therefore is costly to manufacture, it is time consuming to screw the cap member 50 to the port structure, and it does not provide an audible signal when the cap member is safety secured to the port structure. This later feature is provided by the second and third embodiments of this invention.

Second Embodiment of the Invention

Figure 5:
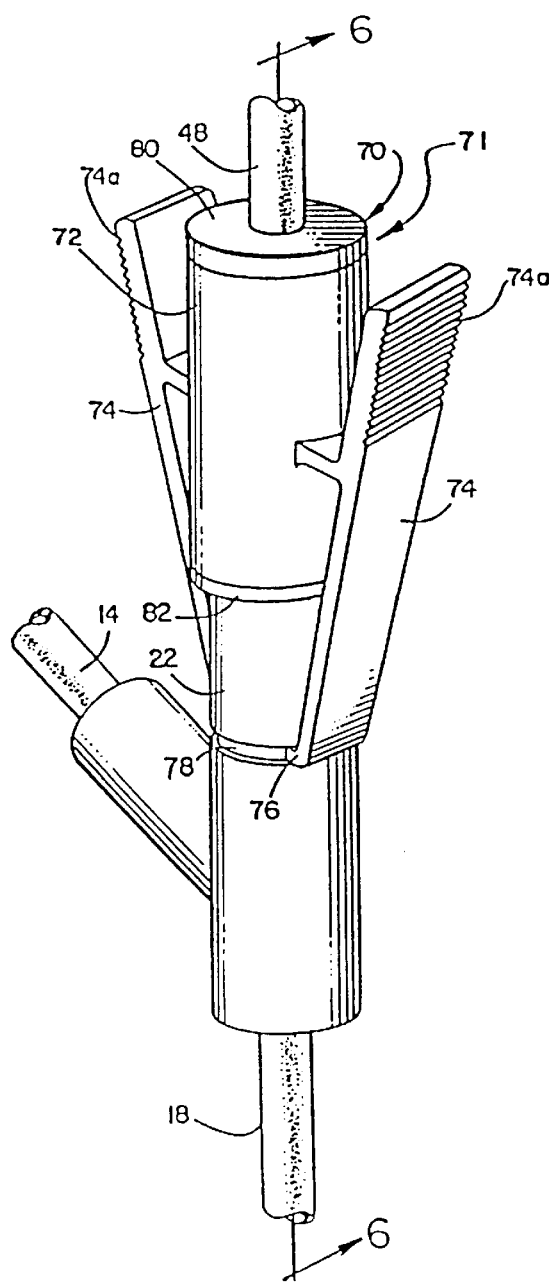
FIG. 5 is a perspective view of the second embodiment of the medical connector of the the present invention which employs a snap-on type means for securing the cap member to the port structure.
Figure 6:
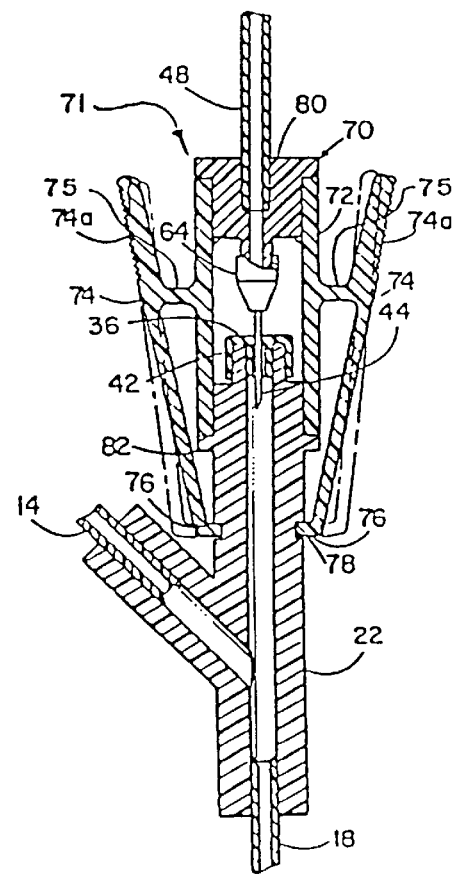
FIG. 6 is a cross-sectional view of the connector shown in FIG. 5 taken along line 6—6 of FIG. 5.

The second embodiment of the present invention, connector 71, is shown in FIGS. 5 and 6. In this embodiment a cap member 70, similar to cap member 50, is simply snapped onto the piggyback connector 16. The snap-on type locking mechanism of this connector 71 is easier to use and less costly to manufacture than the slip-on/twist type of the first embodiment.

In this embodiment, the cap member 70 includes a hollow cylindrical element 72 which carries on its exterior two clips 74 which have catch tips 76 that snap into a groove 78 in the external wall of the conduit 22. The clips 74 are mounted by hinges 75 to the element 72, and are integral with the element 72. A plug assembly 80 carries the tubing 48 and the needle 44, which is mounted on an adapter 64 such as shown in FIG. 4. This plug assembly 80 is glued or otherwise bonded to the open end of the cylindrical member 72. The cap member 70, including clips 74 and hinges 75, are molded from the same material, for example, nylon, which is a material having the desired resiliency.

To attach the cap member 70, one simply slips the member 70 over the conduit 22. The clips 74 bend outwardly slightly and, when the catch tips 76 of the clips are opposite the groove 78, the clips snap in place as shown in solid lines in FIG. 6. The centrally mounted needle 44 is guided into the center of the seal 36 by the cap member 70, which, like a telescope, slides over the tubular conduit 22. There is shoulder 82 which serves as a stop to limit the movement of the cap member 70. This shoulder 82 brings the catch tips 76 of the clips into registration with the groove 78. The hinges 75, being of the same material as the clips 74, provide an internal bias or spring action due to the resiliency of the material from which these clips and hinges are made. Consequently, the clips 74 snap into a locking position, locking the cap member to the conduit 22 when the catch tips 76 are in registration with the groove 78. To release the cap member from the piggyback connector 16, the clips 74 are simply depressed and the cap member 70 is removed.

One of the features of the slip-on type locking mechanism is that with one simple inwardly push the needle 44 is inserted directly into the center of the seal 36 and the cap member is locked to the port structure. Another feature of this connector 71 is that when the tips 76 of the clips snap into the groove 78 a "click" sound is made by the tips striking the body of the cap member. With repeated use, however, the hinges 75, due to internal stress produced in the nylon material, loose some of their spring action. Consequently, the tips 76 are not held with sufficient force in the groove 78, nor do they strike the body of the cap member to produce the desired "click" sound. Moreover, the material will eventually crack along the flex line of the hinge and a break will occur. The reliability of this connector 71 is substantially improved by the third embodiment of this invention which employs a unique locking mechanism.

Third Embodiment of the Invention

Figure 7:
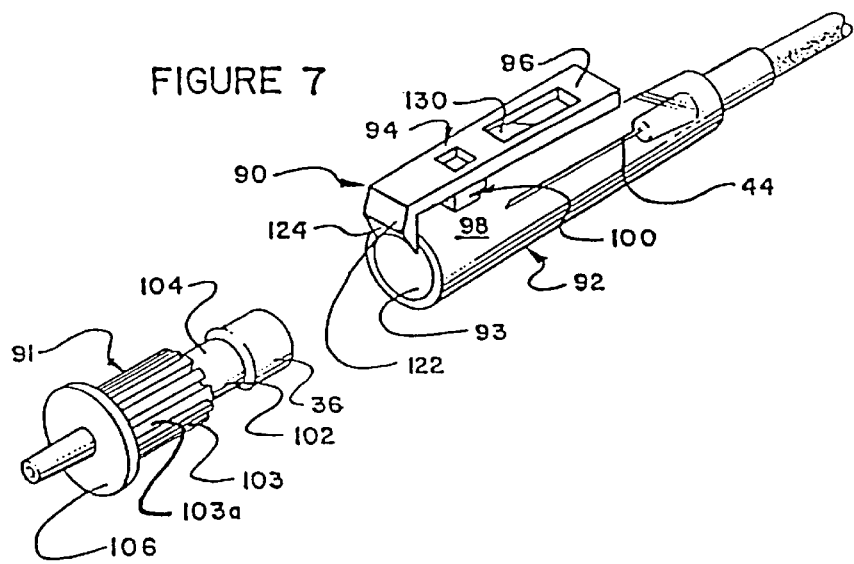
FIG. 7 is an exploded perspective view of the third embodiment of the medical connector of the present invention which employs a snap-on type means for securing the cap member to the port structure.

As shown in FIG. 7, the third embodiment of this invention, connector 90, includes a sealed port structure 91 and a cap member 92 having a locking mechanism 94 for detachably securing the cap member 92 to the port structure 91. The cap member 92 is similar to the cap members of the other embodiments and houses within its cavity 92a (FIG. 8) the needle 44. The cavity 92a has a tapered side wall 93 to better direct the needle 44 into the center of the seal 36.

The port structure 91 is a tubular conduit 102 having, at one end, a reduced diameter nipple 104 over which the seal 36 fits and, at the other end, a tapered barrel 103. The seal 36 is of the same type employed in conventional devices such as shown in FIG. 2. Material is removed from the barrel 103 to reduce cost. This results in the formation of flutes 103a in the barrel 103. At the base of the barrel 103, adjacent the end of the port structure 91, is an annular, disk-like piece which provides a lip 106. When the cap member 92 is placed over the port structure 91, a handle 96, which is a component of the locking mechanism 94, engages this lip 106. The handle 96 is hinged to the body 98 of the cap member by a two component hinge 100.

Figure 14:
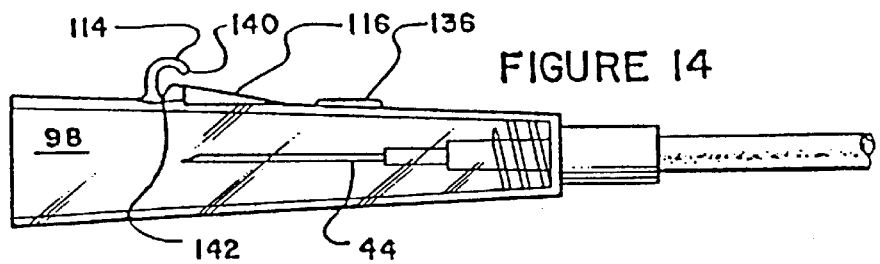
FIG. 14 is a side elevational view of the cap member with the handle of the locking mechanism removed.
Figure 15:
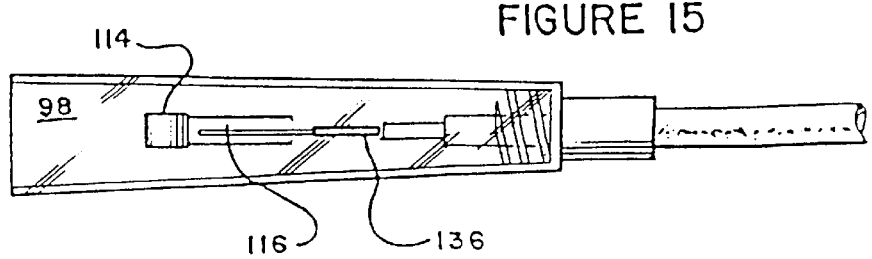
FIG. 15 is a top plan view of the cap member with the handle of the locking mechanism removed.

As best shown in FIGS. 14 and 15, a hook 114 is one component of the hinge 100 and the other component of the hinge is a crossrod 108 (FIG. 18) carried by the handle 96. The hook 114 projects outwardly from the body 98 of the cap member and has adjacent to it a ramp 116, which as shown in FIG. 18, holds the crossrod 108 when the handle 96 is attached to the body of the cap member. A section of the crossrod 108 is cut away to provide a miter slot 118 which engages the ramp 116.

Figure 8:
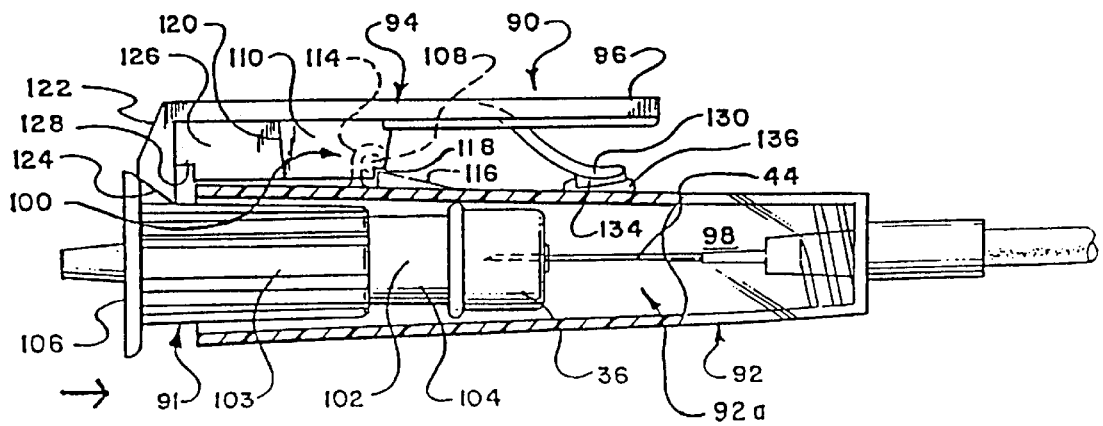
FIG. 8 is a side elevational view, with sections broken away, of the embodiment shown in FIG. 7. In this FIG. 8 the handle of the locking mechanism attached to the cap member just engages the lip of the port structure.
Figure 9:
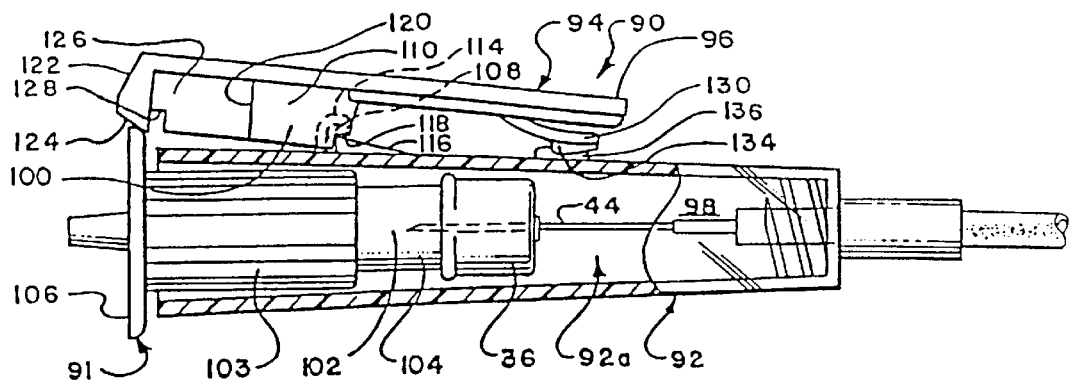
FIG. 9 is the same view as shown in FIG. 8, except the handle of the locking mechanism is flexed and just about to snap into locking engagement with the lip of the port structure.
Figure 10:
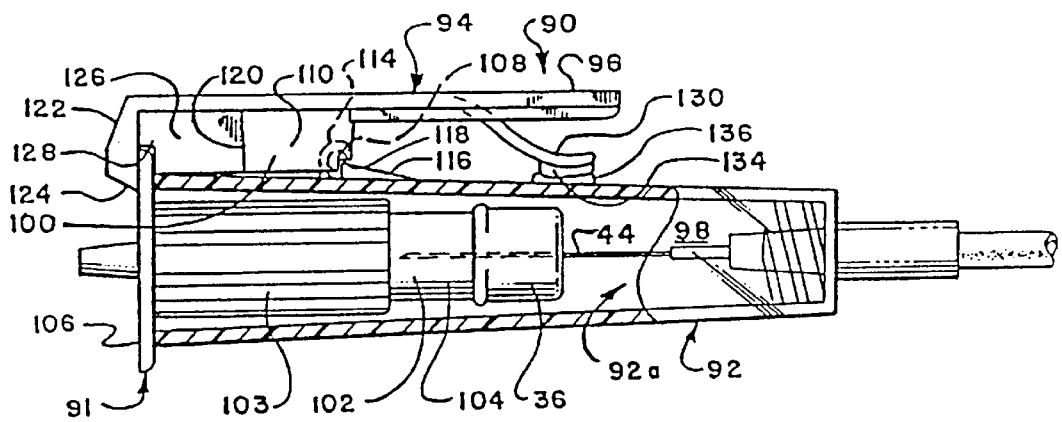
FIG. 10 is the same view as shown in FIGS. 8 and 9, except the handle of the locking mechanism is now engaging the lip of the port structure in the locking position.
Figure 10A:
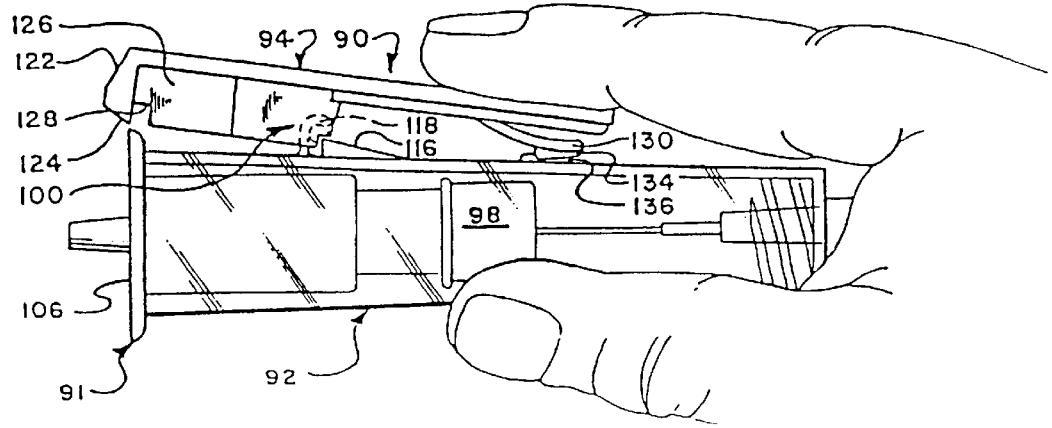
FIG. 10a is the same view as shown in FIGS. 8, 9 and 10, except the handle of the locking mechanism is flexed to permit removal of the cap member from the port structure.
Figure 11:
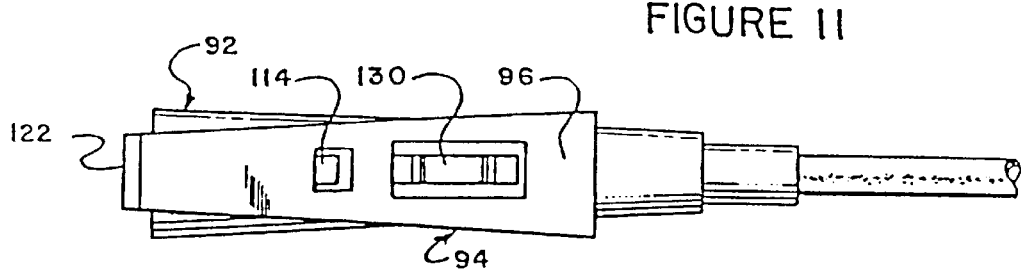
FIG. 11 is a top plan view of the cap member.
Figure 12:
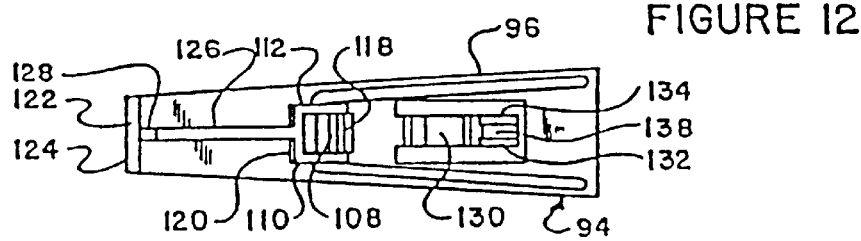
FIG. 12 is a bottom view of the handle of the locking mechanism shown in FIGS. 8 through 11.
Figure 13:
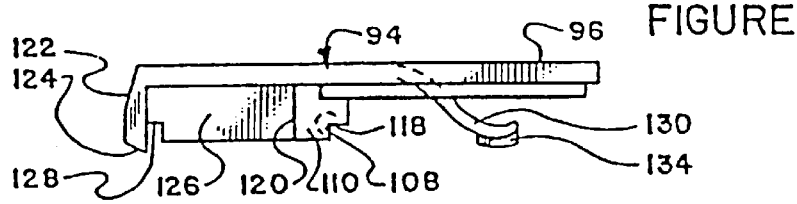
FIG. 13 is a side elevational view of the handle of the locking mechanism.

The handle 96 is best shown in FIGS. 12 and 13. It has a pair of spaced apart plates 110 and 112 extending downwardly from the underside of the handle and the crossrod 108 is disposed between these plates, with the opposed ends of the crossrod being integral with the plates. Opposite the crossrod 108 and parallel to it is a third plate 120, which is integral with the underside of the handle 96 and is at a right angle to and connects with the forward ends of the plates 110 and 112. Disposed on the underside of the handle 96 between the catch tip 122 and the plate 120 is a clapper bar 126. The clapper bar 126 produces the "click" sound when it strikes the body 98 of the cap member. This clapper bar 126 extends away from the plate 120 at a right angle and is integral, at one end of the handle, with the catch tip 122 and, at its opposite end, with the plate 120. The leading edge 124 of the catch tip 122 is beveled to facilitate the slippage of this tip up and over the lip 106 which is also beveled. At the point where the clapper bar 126 merges with the inside of the catch tip 122, there is a notch 128, which, as shown in FIG. 10, receives the lip 106 when the handle 96 is in the locking position. At the rearend of the handle 96 is a leaf spring 130 which has one end free and its opposed end integral with the handle 96. At the free end of the leaf spring 130 are two spaced apart tracks 132 and 134 (FIG. 12). When the handle 96 is attached to the body of the cap member as shown in FIGS. 8 through 10, a finger 136 on the body 98 of the cap member is received within the channel 138 between the tracks 132 and 134. On the underside of the handle 96 are two downwardly projecting (unnumbered) (FIG. 12) which provide structural rigidity to the handle.

The way in which the handle 96 is pivotably connected to the cap member 92 by the two component hinge 100 is illustrated by FIGS. 16 through 19. To attach this handle 96 to the body 98 of the cap member, first one positions the handle over the body of the cap member opposite the hook 114 and then moves the handle into contact with the cap member so that the crossrod 108 touches the rearend of the ramp 116. The spring 130 is depressed at this time. Next, the handle 96 is moved towards the left, as shown in FIG. 17, with the crossrod 108 sliding up the ramp 116 until it engages the leading edge 140 of the hook 114. The dimension between the edge 142 of the ramp 116 and the edge 140 of the hook 114 is less than the diameter of the crossrod 108. Consequently, the hook 114 must flex slightly upwardly in a counterclockwise direction, as viewed in FIG. 17, until the crossrod 108 clears the edge 142 of the ramp and snaps into the position shown in FIG. 18. The hook 114 thus returns to the unflexed condition shown in FIG. 18, wrapping around the crossrod 108. The miter slot 118 then engages the edge 142 of the ramp, with this edge abutting the junction 118a of the slot 118 (FIG. 18). The ramp 116 thus holds the crossrod 108 in position, preventing the handle from becoming dislodged from the hook 114 and preventing the handle 96 from tilting to-and-fro about its longitudinal axis. When the handle 96 is so mounted to the body 98 of the cap member, the finger 136 slips into the channel 138 between the tracks 132 and 134 and holds the rearend of the handle so that it does not tend to move laterally. The handle 96 is, however, free to pivot about the hinge 100.

Unlike the hinges 75 of the second embodiment of this invention, the two component hinge 100 does not break due to fatigue. Thus, in accordance with one feature of connector 90, the handle 96 may be moved between a locked position (FIG. 10) and unlocked position (FIG. 8) as often as one wishes without breaking. At the same time, the handle 96, connecting with the body 98 of the cap member 92, generates a "click" sound when the cap member is locked to the port structure 91. This "click" sound, as best illustrated in FIGS. 9 and 10, occurs when the handle 96 moves between the flexed position shown in FIG. 9 and the locked position shown in FIG. 10.

The connector 90 is highly reliable under actual hospital working conditions, and the way connector 90 is used is best shown in FIGS. 8 through 10a. First, the nurse inserts the end of the port structure carrying the seal 36 into the open mouth 93 of the cap member 92 to bring the lip 106 into engagement with the catch tip 122 of the handle 96 as shown in FIG. 8. As this is done, the tapered side wall 93 of the cap member and the tapered barrel 103 slide along each other to direct the needle 44 into the center of the seal 36. Simultaneously, the beveled edge 124 of the catch tip rides over the beveled lip 106 until the lip just engages the underside edge of this tip as shown in FIG. 9. This causes the handle 96 to rotate in a clockwise direction as viewed in FIG. 9, with the crossroad 108 turning while in the grasp of the hook 114. There is enough clearance between the miter slot 118 and the edge 142 of the ramp to allow the crossrod to turn sufficiently so the catch tip 122 clears the lip 106. Thus the handle 96 pivots about the hinge 100, depressing the spring 130. With the handle 96 and lip 106 in this position and the spring 130 depressed, as soon as the lip 106 clears the edge of the catch tip 122, the spring rotates the handle in a counterclockwise direction, moving it to the position shown in FIG. 10 with ample force so that the clapper bar 126 strikes the body 98 of the cap member to produce the "click" sound. This "click" sound is the audible signal which the nurse may rely upon to indicate that the cap member 96 is locked to the port structure 91. Under certain hospital conditions, particularly in the intensive care unit where there is not a great deal of light, this is an important feature because it provides additional assurance that the cap member 92 is locked to the port structure 91.

As shown in FIG. 10, with the handle 96 in this locked position, the needle 44 has penetrated the central portion of the seal 36, directed by the tappered sidewalls of the cavity 92a and the barrel 103. Medication now flows through the connector 90 into the patient. Note, the handle 96 is not depressed as the cap member 92 is slid over the port structure 91. To remove the cap member 92, the handle 96 is depressed, moving it to the position shown in FIG. 10a. With the handle 96 in this position, the cap member 92 is pulled off the port structure 91.

Except for the seal 36, the connector 90 is made entirely of a transparent plastic. The use of a transparent plastic is preferred because this allows the nurse to see that the needle 44 is correctly inserted into the seal 36, and thus provides additional safety. Also, the use of plastic makes the connector 90 a low cost, disposable item. The plastic most suitable is a polycarbonate made by Cyrolite Industries in Azusa, Calif. sold under the tradename Cyrolite. This plastic, which is commonly employed to make medical devices, has been approved for such uses by the United States Federal Drug Administration.

The connector 90 is particularly adapted to be used in a variety of different applications. For example, as illustrated in FIG. 20, it may be connected directly in line with a container 144 of medication to be supplied intravenously to a patient. In this instance, the cap member 92 has a tube 146 extending from it which has at its one end a male component 148 of a conventional luer lock connector. This male component 148 engages and locks with a mating female luer component 150 attached to the end of a line 146 extending from the container 144. In a similar manner, the port structure 91 has extending from it a tube 154 which has at its end a female luer component 158 of a second luer lock connector. The male component 156 of this second luer lock connector is attached to the end of a tube 160 that is connected to a needle inserted into the vein of the patient. The luer lock connectors may be obtained from Burron Medical, Inc. in Bethlehem, Pa.

Figure 21:
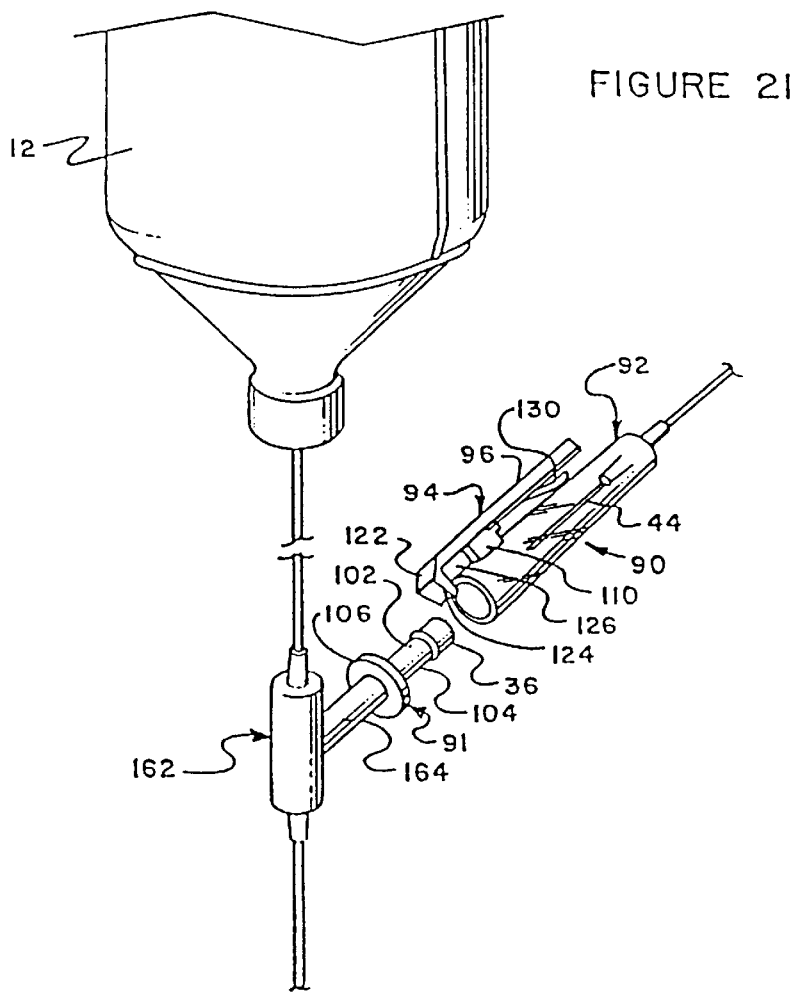
FIG. 21 is a perspective view of a medical connector like that shown in FIG. 7, except the port structure has the lip which engages the handle of the locking mechanism as an integral part of a conventional piggyback connector.

FIG. 21 illustrates the connector 90 integrated into a conventional piggyback connector 162. The branch line 164 from the piggyback connector 162 has attached to it and integral therewith the port structure 91 including the lip 106 that engages the catch tip 122 of the locking mechanism 94. Thus, a conventional feeding system 10 employing a piggyback connector may be modified by simply including a lip 106 adjacent the seal 36. This lip 106 will then serve as the site for detachably connecting the cap member 92 to the piggyback connector 162.

Figure 22:
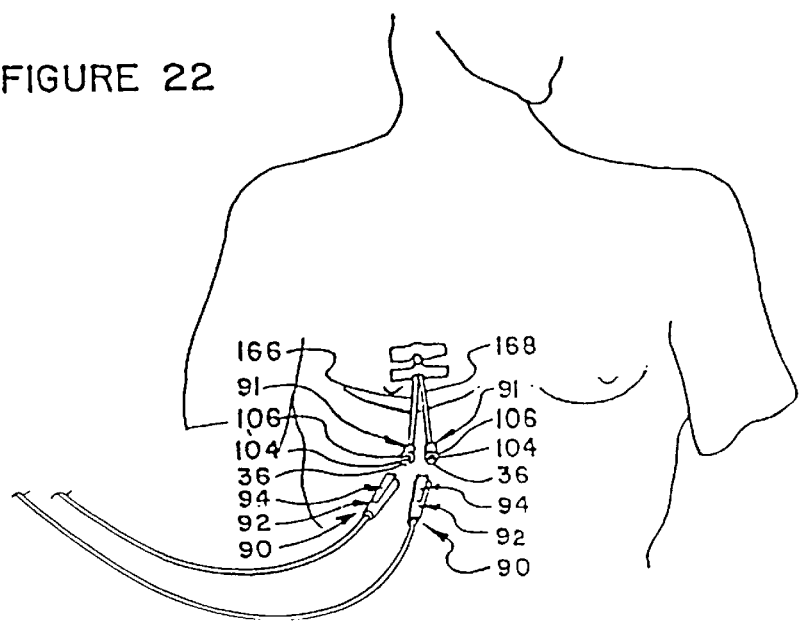
FIG. 22 is a schematic view showing a medical connector of the type shown in FIG. 7 designed to introduce medication into a patient's chest.

The connector 90, as shown in FIG. 22, also lends itself to be used with central venous catheters which are inserted into the chest of the patient. Frequently, patients under home care use such catheters, and consequently, even simpler and safer devices and techniques must be employed. However, a serious problem with such catheters is the way the ends of the lumens or tubes 166 and 168 extending from the patient are sealed. Presently, the ends of these tubes 166 and 168 are sealed using conventional luer locks. When it is time for the patient or the nurse to introduce medication into the catheter, an intermediate portion of the tubes 166 and 168 must be clamped while being connected to the source of medication so that air is not drawn into the blood stream of the patient. Any large intake of air into the patient's blood stream will seriously injure or even kill the patient. With children, even a small amount of air may be fatal. That is why clamps are used to close off the tubes 166 and 168 until the connection is made with the source of medication. This results in the tubes 166 and 168 wearing out, requiring that they be repaired. Not only is this a dangerous system, but it is extremely inconvenient for the patient or nurse to use.

As illustrated in FIG. 22, the connector system 90 overcomes these difficulties by simply having at each of the respective ends of the tubes 166 and 168 port structures 91. When the patient needs medication, he or she simply connects two of the cap members 92 to the respective port structures 91, and when finished, disconnects the cap members. The medication is fed by the needles 44 through the seals 36 and into the respective tubes 166 and 168. The cap members 92, when detached, withdraw the needles 44 from the seals 36, which are self sealing. Thus, the nurse does not need to clamp off the tubes 166 and 168 nor is periodic repair of the tubes required. Since the seal 36 is self-sealing, upon removal of the cap member 92 there is no danger of air being drawn through the port structure 91 into the patient's blood stream. Consequently, connector 90 is both safer and more convenient to use than the conventional central venous catheters.

The connector 90 is also adapted to be used repeatedly without damaging the seal 36. Thus it is even more suitable for such applications as illustrated in FIG. 22 than conventional devices, because of the accuracy with which the needle 44 may be repeatedly directed into the center of the seal 36. When the needle 44 is repeatedly stuck into and withdrawn from the seal 36, the seal will have numerous holes in it and begin to develop a "swiss cheese" like appearance. Eventually, a core is cut away from the seal by several of these holes interconnecting, rendering the seal useless because it is no longer self-sealing. Consequently, the seal would have a very short life. By carefully controlling the dimensions of the molds used to make connector 90, the cap member 92 and port structure 91 will be precision made parts. Consequently, with repeated use, the needle 44 will essentially always penetrate the same hole in the seal 36, thus avoiding the "coring" problem.

Fourth Embodiment of the Invention

Figure 23:
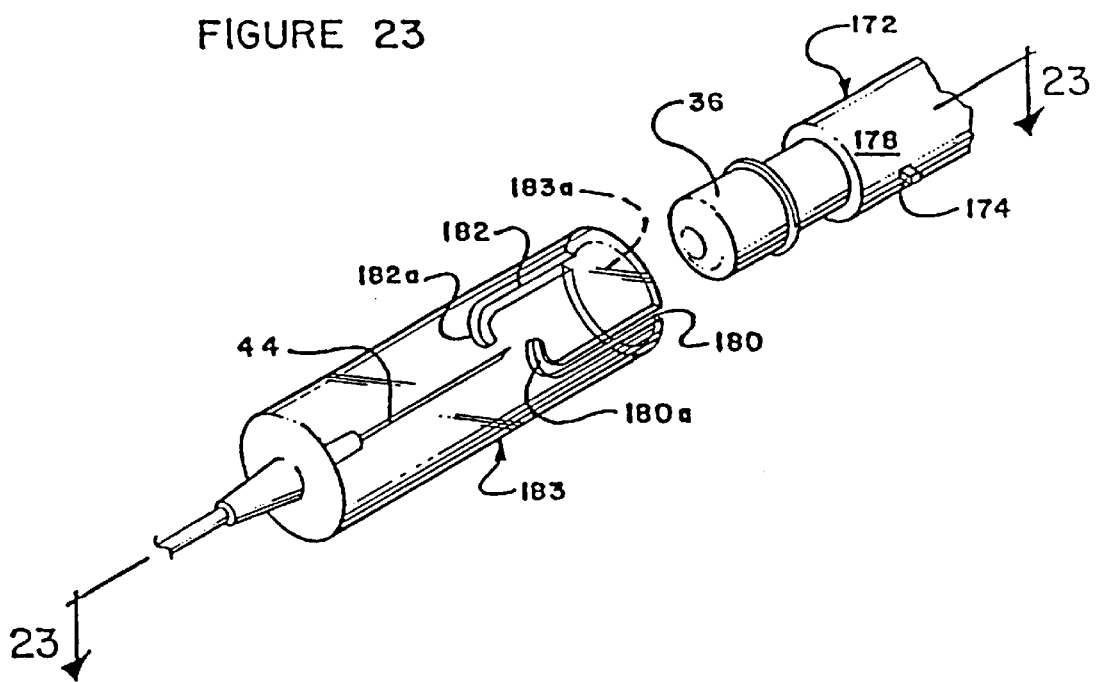
FIG. 23 is a perspective view of a fourth embodiment of the medical connector of this invention which employs a slip-on/twist lock type means for securing the cap member to the port structure.
Figure 24:
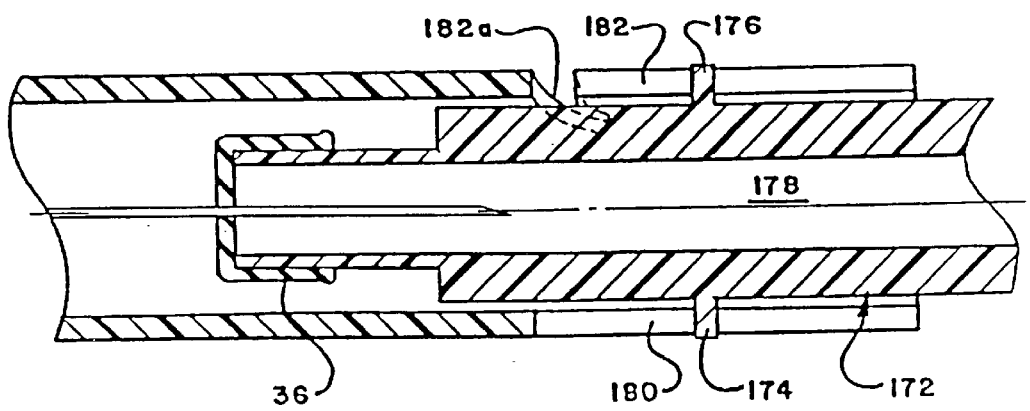
FIG. 24 is an enlarged cross-sectional view taken along line 24—24 of FIG. 23, showing the cap member being connected to the sealed entry port structure.

The fourth embodiment of this invention, the connector 170, is illustrated by FIGS. 23 and 24. In connector 170 the port structure 172 is similar to that shown in the other embodiments except it has a pair of pins on opposite sides of its body 178 which co-act with J-type slits 180 and 182 in the sidewall of a cap member 183 housing the needle 44. These J-type slits 180 and 182 are opposed to each other and provide a guideway for the pins 174 and 176 which slide along these slits as the port structure 172 matingly engages the cap member 183.

To use this connector system 170, the nurse aligns the port structure 172 with the open mouth 183a of the cap member so that the pins 174 and 176 are in alignment with the entryway to the J-type slits 180 and 182. Then the nurse pushes the port structure 172 into the open mouth 183a, sliding the port structure into the cavity within the cap member 183. The pins 174 and 176 first engage the entryway of the J-type slits 180 and 182 and then slide along the slits until they reach the base of the slits. At this point, the nurse twists or rotates the cap member 183 and port structure 172 in counter-rotating directions so that the pins 174 and 176 will then slide respectively into the hooks 180a and 182a of the slits and be secured. This embodiment does not provide an audible signal upon locking the cap member 183 to the port structure 172, but is very economical to manufacture.

Function of the Cap Member and Port Structure

As will be appreciated from the above description, the cap member provides several functions in a single structure. (We will no longer refer by number to any one of the components of the invention since we are now discussing in general how the cap member and port structure function to provide the attributes of safety and convenience.) First, the cap member surrounds the needle and provides a housing in which the needle is lodged safely so that needle sticks are avoided. Second, because the needle is so lodged within the housing, if the nurse did, for example, lay the cap member on the patient's bed, the needle would not come into direct contact with the bedding which might be infested with harmful bacteria. Thus, this arrangement of the needle deep within the cavity in the cap member provides protection for the patient against bacterial contamination and protection for the nurse against accidental needle sticks.

The port structure also provides more than one function. First, it serves as the site to attach the cap member, and, by means of a simple locking element such as a lip, thread, groove, pin or the like, provides an economical way to modify the conventional piggyback connector so that it may be used with the cap member. Second, the combination of a self-sealing seal and adjacent element that locks with the cap member provides a simple way to modify connectors so that they have enhanced safely and convenience.

The cap member and port structure function in combination to direct the needle into the center of the seal, lock these pieces together, and enable quick connection. The nurse or patient simply aligns the sealed end of the port structure with the open mouth of the cap member and pushes the two pieces together. The internal wall of the cap member and the exterior wall of the port structure engage to align the two pieces so that their respective axes coincide, guiding the needle into the center of the seal as they are pushed together. Consequently, the needle does not scrape the inside wall of the port structure so that particles of plastic are not introduced into the patient's blood stream and the coring problem is virtually eliminated. The cap member and port structure each carry elements of a locking mechanism which engage and lock the pieces together when the needle has pierced the seal, preventing accidental disconnect. Although other geometric forms may be employed, quick connection is facilitated by the cylindrical configuration of the walls of the cap member and port structure and the circular open mouth of the cavity. In particular, the first through third embodiments of this invention are very quickly connected because no extra step is required to align the cap member and port structure. All that the nurse need do is insert the port structure into the open mouth without any special concern for their relative positions, and, when using the second and third embodiments, simply push these two pieces together until the locking mechanism engages. When using the first or fourth embodiments, the extra step of rotating the two pieces relative to each other is required to engage the locking mechanism. When using the forth embodiment, the pins must also first be aligned with the entryways to the J-slits prior to pushing the port structure into the cavity in the cap member.

Because of the features embodied in the cap member and port structure, this invention may be used under normal hospital conditions without creating any additional work for the nurse, while substantially reducing the likelihood of harm to the patient due to carelessness and protecting the nurse against infection and making his or her job easier and faster.

SUMMARY

In summary: Our connector is safe because (a) the needle is recessed deeply within the cap member and, therefore, is not likely to be contaminated by bacteria, (b) the cap member and port structure upon engagement guide the needle into the center of the seal, avoiding scraping particles from the inside wall of the port structure, (c) the cap member, housing the needle safely within it, protects the nurse against needle sticks, and (d) the locking of the cap member and port structure together prevents accidental disconnects and (e) the "click" signals the nurse when the connector system is locked securely in position. Our connector is convenient to use because (a) the walls of the cap member and port structure, interacting with each other, provide a guideway for quick connection, (b) the locking mechanism eliminates the burdensome and time consuming task of taping, and (c) the connector is very simple to use so that it is ideal for home care of patients.

SCOPE OF THE INVENTION

The above description presents the best mode contemplated of carrying out the present invention as depicted by the four embodiments disclosed. The combination of features illustrated by these embodiments provide the safety and convenience of this invention. This invention is, however, susceptible to modifications and alternate constructions from the embodiments shown in the drawing and described above. Consequently, it is not the intention to limit it to the particular embodiments disclosed. On the contrary, the intention is to cover all modifications and alternate constructions falling within the scope of the invention as generally expressed by the following claims.

We claim:

1. A medical connector for selectively transferring a fluid from one location to another, said connector comprising:

a first connector member having a proximal end;

a resilient, pre-slit resealable septum positioned at said proximal end of said first connector member, said septum presenting a flat, swabbable outer surface;

a second connector member for connection to said first connector member for establishing a fluid flow between said members, said second connector member having a body with a hollow proximal end, said body adapted for extension over said proximal end of said first connector member, and a hollow tube, said hollow tube connected to said body, said hollow tube having a free end positioned within said hollow proximal end of said body, whereby said end of said hollow tube is recessed within said proximal end of said body, and whereby when said body is extended over said proximal end of said first connector member, said hollow tube penetrates said septum.

2. The medical connector in accordance with claim 1, wherein said body is generally cylindrical in shape.

3. The medical connector in accordance with claim 1, wherein said hollow tube has a second end in communication with a fluid line extending from said second connector member.

4. The medical connector in accordance with claim 1, further including means for selectively locking said first connector member to said second connector member in a position in which said hollow tube extends through said septum.

5. A two-piece medical connector for selectively establishing flow of medication, comprising:

a port member, said member having an end with a resilient, pre-slit resealable and swabbable septum extending there across; and an engaging member for selective engagement with said port, said engaging member having a body defining a hollow chamber, said body having an end with an opening therein leading to said chamber, a hollow tube having a free end, said hollow tube extending from said body such that said free end of said hollow tube is positioned in said chamber, said opening sized so that said body may be selectively extended over said port member, whereby said hollow tube penetrates said septum for establishing a flow of medication between said engaging member and said port, and wherein said septum raseals when said hollow tube is removed.

6. The medical connector in accordance with claim 5, wherein said engaging member has a fluid line extending therefrom, said fluid line in communication with a passage extending through said hollow tube from said free end of said hollow tube.

7. The medical connector in accordance with claim 5, wherein said port member has a chamber positioned distal of said septum and a fluid line extending in communication with said chamber.

* * * * *

(12) EX PARTE REEXAMINATION CERTIFICATE (5836th)
United States Patent
Lopez et al.

(10) Number: US 5,954,708 C1
(45) Certificate Issued: Jul. 31, 2007

(54) MEDICAL CONNECTOR

(75) Inventors: George A. Lopez, Huntington Beach, CA (US); Virgil R. Laul, Dana Point, CA (US)

(73) Assignee: ICU Medical, Inc., San Clemente, CA (US)

Reexamination Request:
No. 90/006,504, Dec. 20, 2002

Reexamination Certificate for:
Patent No.: 5,954,708
Issued: Sep. 21, 1999
Appl. No.: 09/056,974
Filed: Apr. 8, 1998

Related U.S. Application Data

(63) Continuation of application No. 08/473,524, filed on Jun. 7, 1995, now Pat. No. 5,776,116, which is a continuation of application No. 08/424,237, filed on Apr. 19, 1995, now abandoned, which is a continuation of application No. 08/279,247, filed on Jul. 21, 1994, now abandoned, which is a continuation of application No. 08/020,098, filed on Feb. 19, 1993, now Pat. No. 5,344,414, which is a continuation of application No. 07/346,193, filed on Jan. 9, 1987, now abandoned, which is a division of application No. 06/606,679, filed on May 3, 1984, now abandoned, which is a continuation-in-part of application No. 06/543,248, filed on Oct. 19, 1983, now abandoned, which is a continuation-in-part of application No. 06/460,585, filed on Jan. 24, 1983, now abandoned.

(51) Int. Cl.
*A61M 25/16* (2006.01)
*A61M 25/18* (2006.01)

(52) U.S. Cl. ............... 604/533; 604/535; 604/905
(58) Field of Classification Search ............... None
See application file for complete search history.

(56) References Cited

U.S. PATENT DOCUMENTS

| | | | | |
|---|---|---|---|---|
| 3,135,261 A | * | 6/1964 | Carroll | .............. 600/578 |
| 3,171,412 A | | 3/1965 | Braun | |
| 3,986,508 A | | 10/1976 | Barrington | |
| 4,187,846 A | | 2/1980 | Lolachi et al. | |

(Continued)

FOREIGN PATENT DOCUMENTS

| CA | 1105959 | 7/1981 |
|---|---|---|
| DE | 855 319 | 11/1952 |
| EP | 0 367 549 | 10/1989 |
| EP | 0 438 909 | 12/1990 |

OTHER PUBLICATIONS

NITA's Standards of Practice, pp. 71, 72 and Exhibit A showing Nutri–flo Product, vol. 5, Jan.–Feb. 1982.
Baxter Product Brochure, "Closed Drainage Bag", 2 pages.
Baxter Product Brochure, "Urine Sampling Unit", 2 pages.
Travenol Laboratories, Inc., Product ad, "Mini–Bag Underfill Viaflex Containers", 3 pages.
NITA, vol. 7 Mar./Apr. 1984, 6 pages.
Travenol ad, "The Continu–Flo Administration System", 4 pages.
American Journal of Hospital Pharmacy, vol. 26, Jan. 1969, 12 pages.
American Journal of Hospital Pharmacy, vol. 36, Nov. 1979, 7 pages.
American Journal of Hospital Pharmacy, "Evaluation of Piggyback Administration Sets", vol. 34, Dec. 1977, pp. 1315–1323.

*Primary Examiner*—Beverly M. Flanagan

(57) ABSTRACT

Disclosed is a connector for introducing medication into a patient in a safe, convenient way. It comprises a pair of plastic tubular members adapted to be manually pushed together to engage in a male-female relationship, and a locking mechanism that detachably secures the members together. The male member has a sealed entry port at its end, and the female member safely houses within it a needle which centrally pierces the seal of the port upon engagement of the members. Preferably, the locking mechanism provides a "click" sound when it locks the members together.

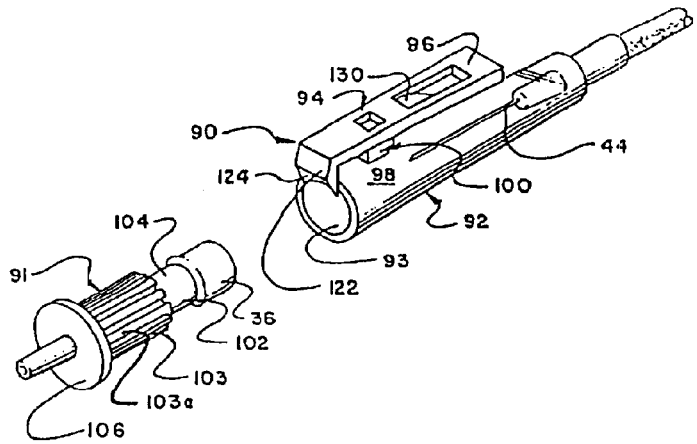

U.S. PATENT DOCUMENTS

| | | |
|---|---|---|
| 4,338,933 A | 7/1982 | Bayard et al. |
| 4,362,156 A | 12/1982 | Feller, Jr. et al. |
| 4,511,359 A | 4/1985 | Vaillancourt |
| 4,759,756 A | 7/1988 | Forman et al. |
| 4,810,241 A | 3/1989 | Rogers |
| 4,834,716 A | 5/1989 | Ogle, II |
| 5,135,489 A | 8/1992 | Jepson et al. |
| 5,281,206 A | 1/1994 | Lopez |
| 5,330,450 A | 7/1994 | Lopez |
| 5,688,254 A | 11/1997 | Lopez et al. |
| 5,776,116 A | 7/1998 | Lopez |
| 5,954,708 A | 9/1999 | Lopez et al. |
| 5,971,950 A | 10/1999 | Lopez et al. |
| 6,290,688 B1 | 9/2001 | Lopez et al. |

\* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–7 are cancelled.

\* \* \* \* \*